(12) United States Patent
Bryant

(10) Patent No.: US 10,515,349 B1
(45) Date of Patent: Dec. 24, 2019

(54) NETWORKED AUGMENTED REALITY AND VIRTUAL VENDING MACHINE

(71) Applicant: Carolyn Bryant, Pasadena, CA (US)

(72) Inventor: Carolyn Bryant, Pasadena, CA (US)

( * ) Notice: Subject to any disclaimer, the term of this patent is extended or adjusted under 35 U.S.C. 154(b) by 0 days.

(21) Appl. No.: 15/957,756

(22) Filed: Apr. 19, 2018

Related U.S. Application Data

(63) Continuation-in-part of application No. 15/912,316, filed on Mar. 5, 2018.

(51) Int. Cl.

| | | |
|---|---|---|
| *G06Q 20/18* | (2012.01) | |
| *G06Q 20/20* | (2012.01) | |
| *G06Q 30/06* | (2012.01) | |
| *H04W 4/02* | (2018.01) | |
| *G06K 7/14* | (2006.01) | |
| *G16H 20/13* | (2018.01) | |
| *H04W 4/35* | (2018.01) | |
| *G06Q 20/02* | (2012.01) | |
| *H04M 1/725* | (2006.01) | |
| *G06F 3/14* | (2006.01) | |
| *G06T 19/00* | (2011.01) | |

(52) U.S. Cl.
CPC .......... *G06Q 20/18* (2013.01); *G06K 7/1404* (2013.01); *G06Q 20/202* (2013.01); *G06Q 20/206* (2013.01); *G06Q 30/0643* (2013.01); *G16H 20/13* (2018.01); *H04W 4/023* (2013.01); *H04W 4/35* (2018.02); *G06F 3/1454* (2013.01); *G06T 19/006* (2013.01); *H04M 1/72594* (2013.01)

(58) Field of Classification Search
USPC ........................................................ 705/18
See application file for complete search history.

(56) References Cited

U.S. PATENT DOCUMENTS

| | | | | |
|---|---|---|---|---|
| 2002/0158133 | A1* | 10/2002 | Conzola | G06Q 30/06 235/462.45 |
| 2007/0198432 | A1* | 8/2007 | Pitroda | G06Q 20/02 705/64 |
| 2018/0121912 | A1* | 5/2018 | Morales | G06Q 20/3829 |

\* cited by examiner

*Primary Examiner* — Garcia Ade
(74) *Attorney, Agent, or Firm* — William J. Benman; Benman, Brown & Williams

(57) ABSTRACT

A first system for maintaining an inventory of goods available for purchase and providing images relating thereto; a second system for wirelessly communicating the images to a mobile communications and computing platform; a third system operationally coupled the mobile communications and computing platform for displaying on the mobile platform at least one of the images of one of the goods on the platform in response to a user's navigation; and a fourth system for effecting a purchase transaction with respect to at least one of the goods correlated with the displayed image. In the augmented reality embodiment, navigation is effected by physically moving the mobile platform relative to the inventive vending machine whereby the products displayed, and the views thereof, change and vary as a function of the relative position of the mobile platform and the vending machine. As an alternative, the physical vending machine is replaced with a virtual vending machine adapted to display the goods on the user's mobile platform in a three-dimensional space.

17 Claims, 12 Drawing Sheets

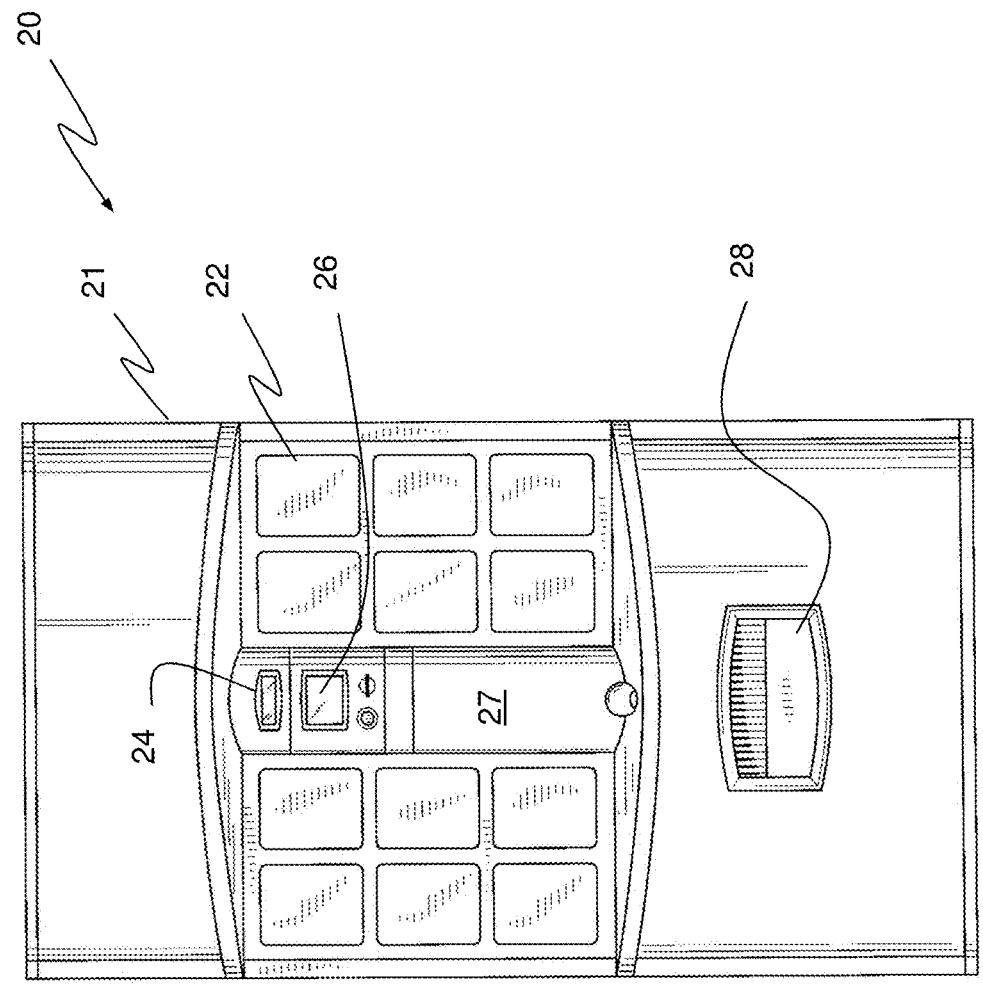

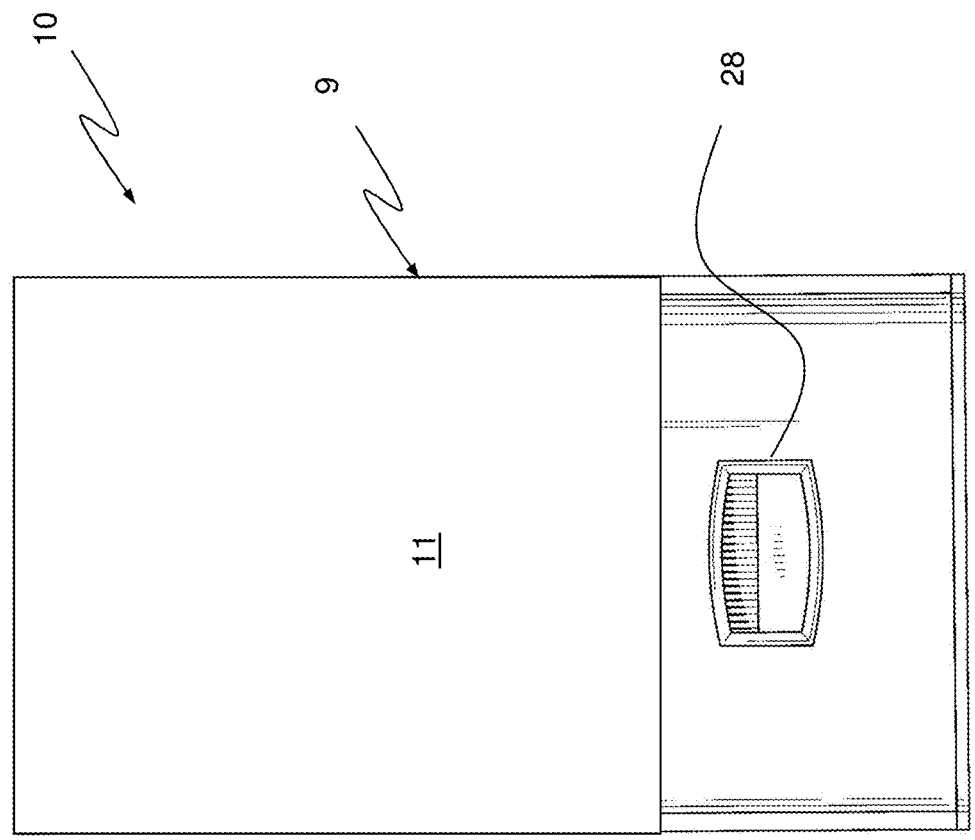

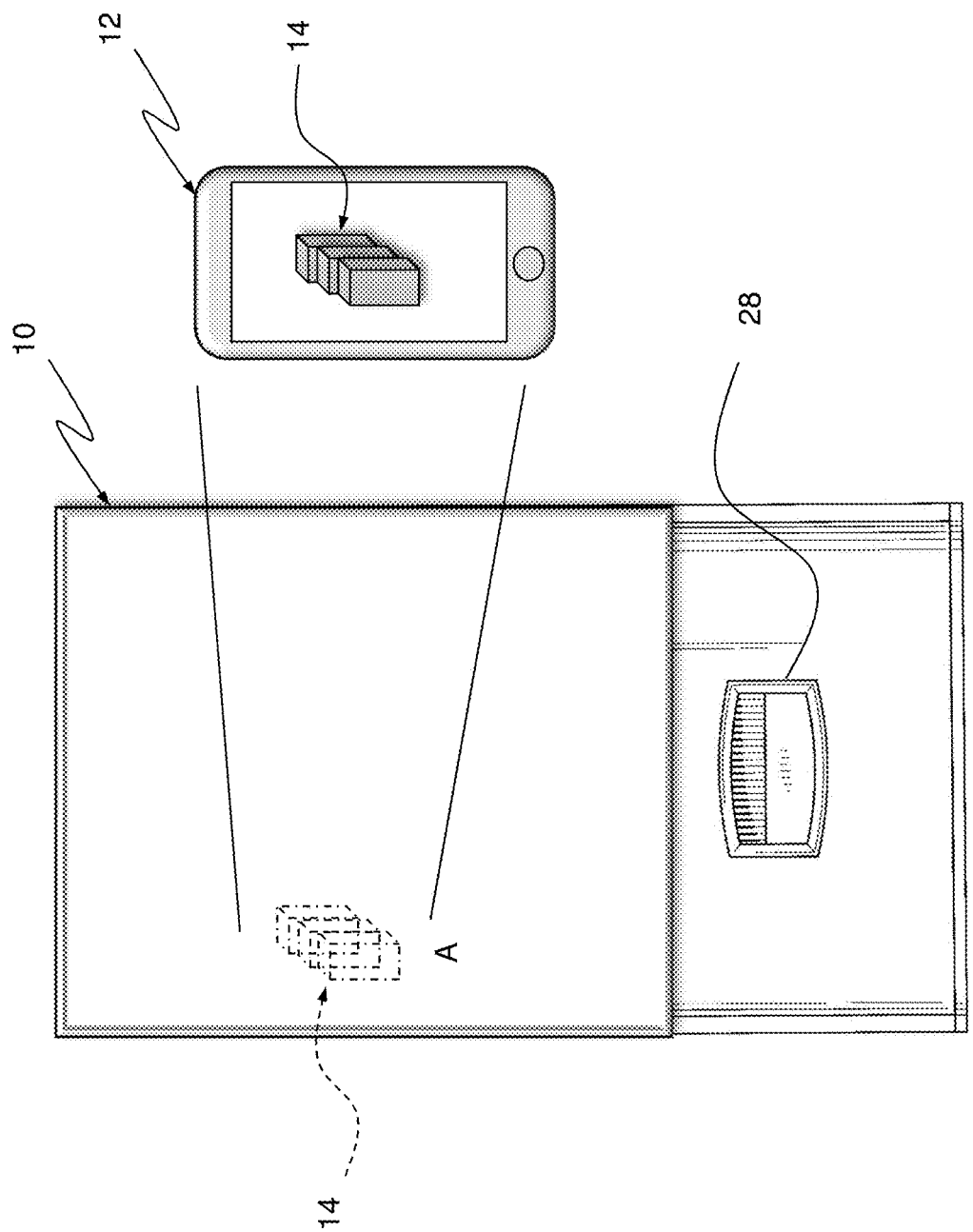

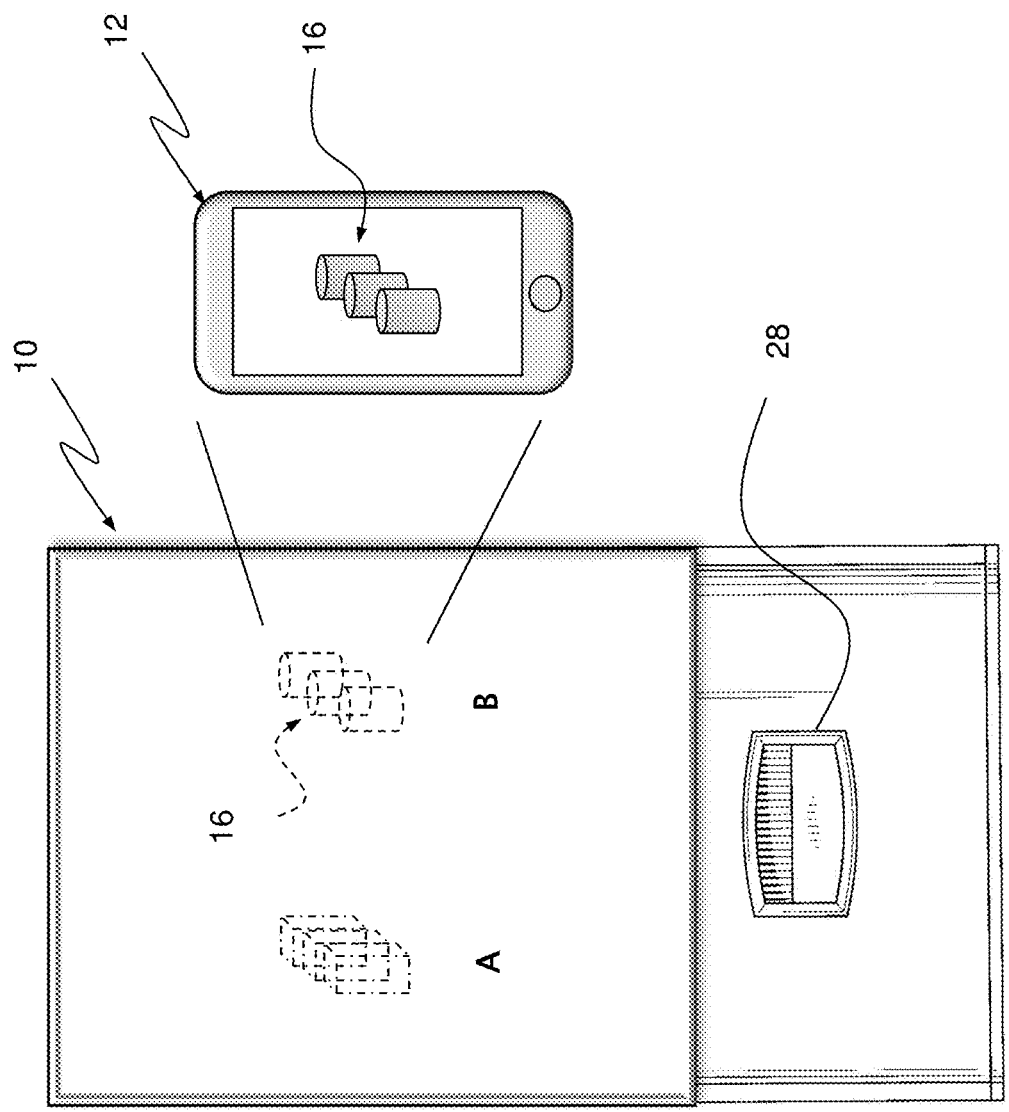

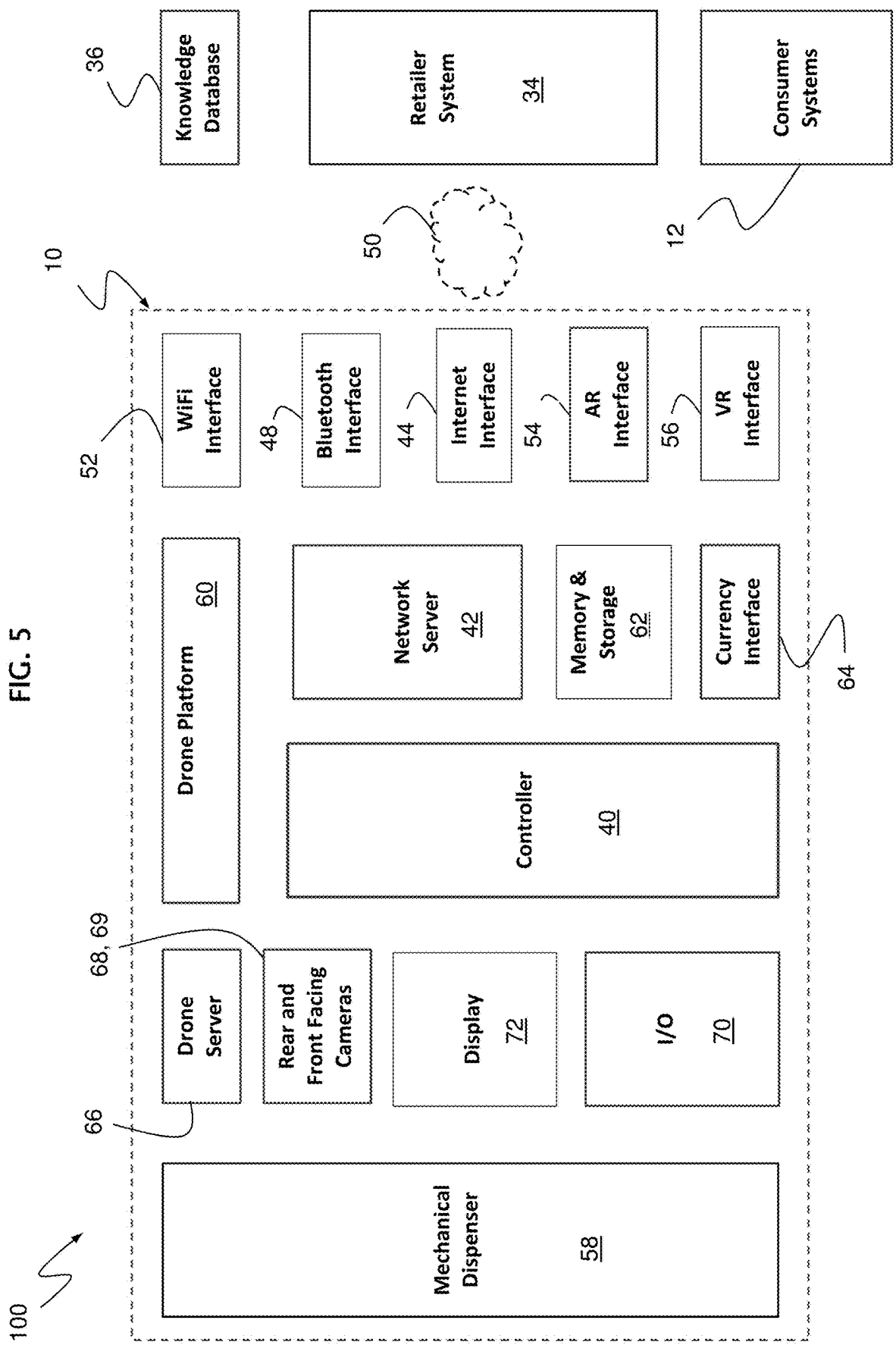

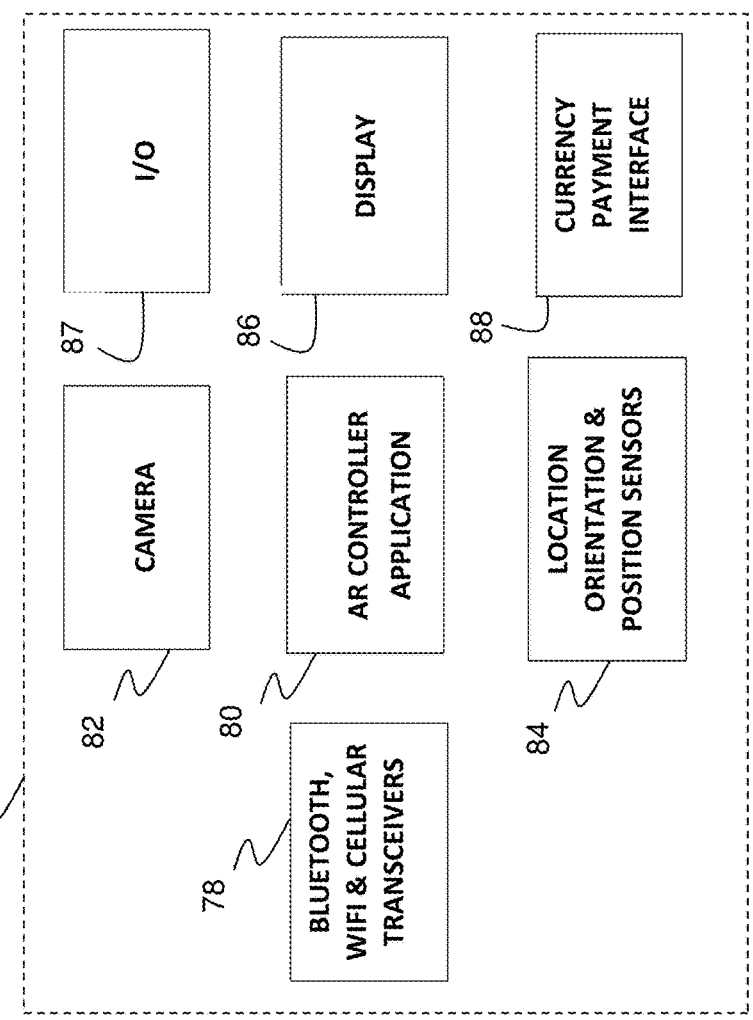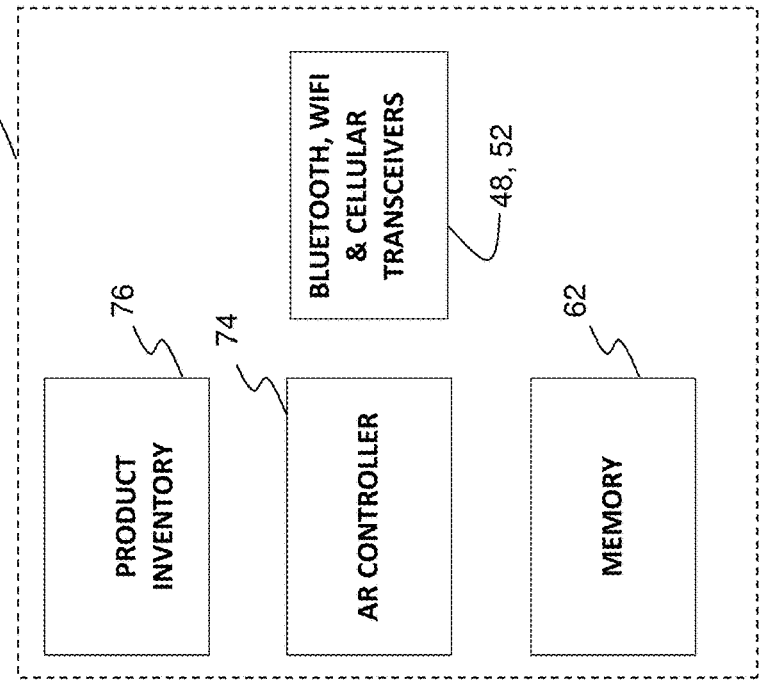

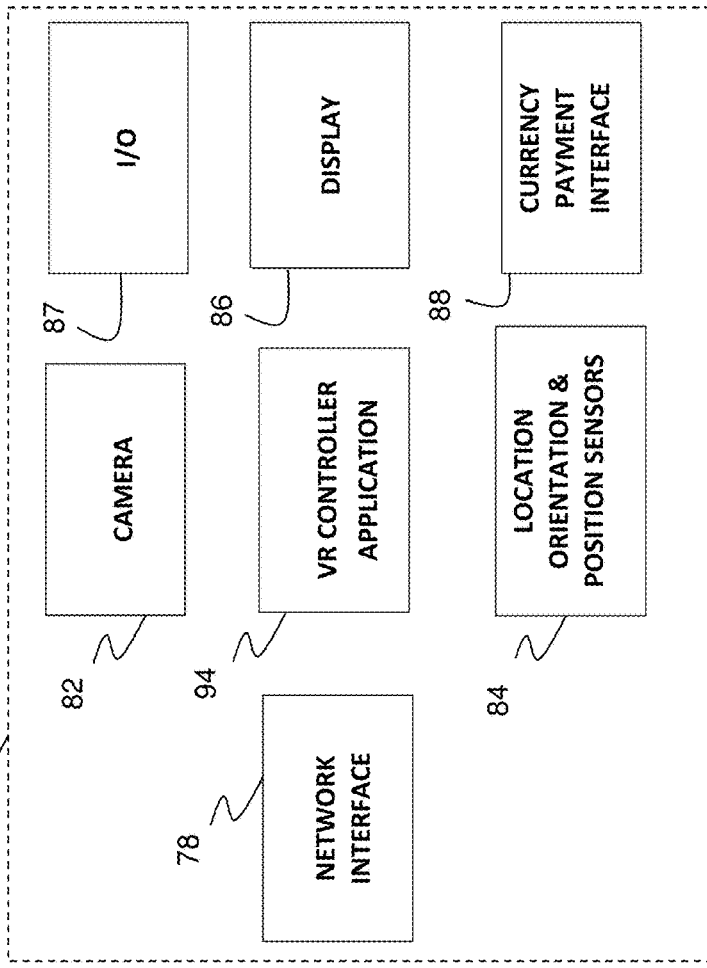
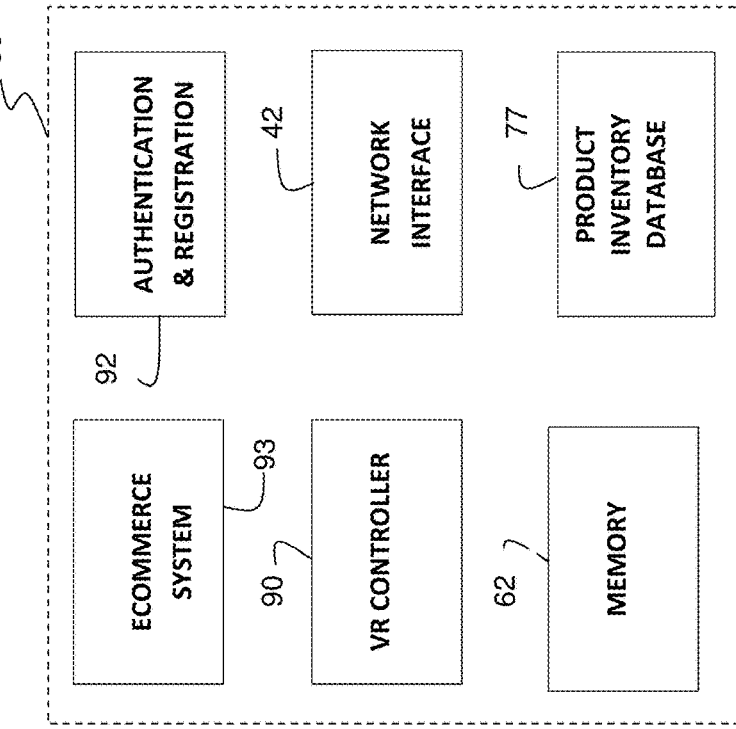

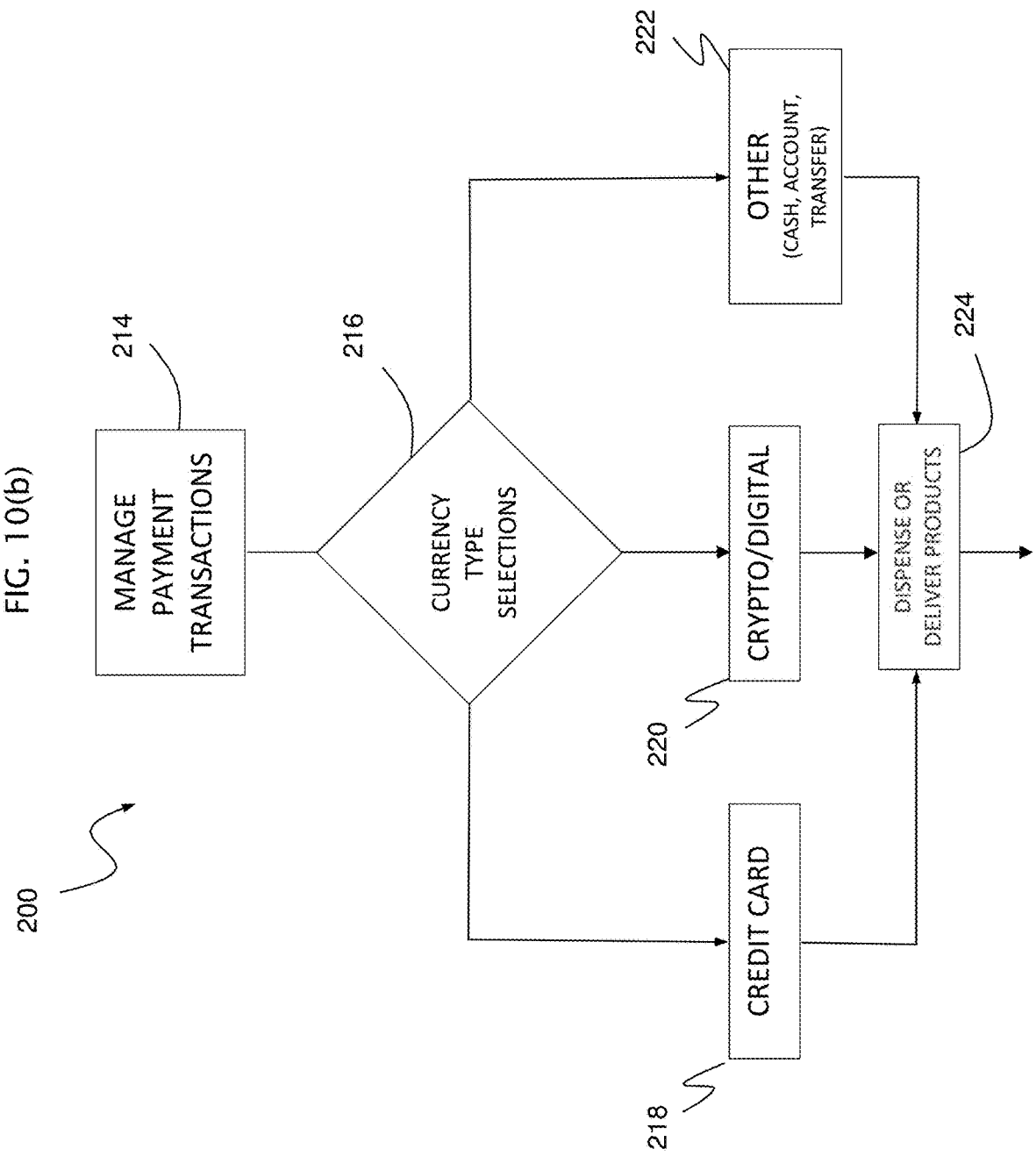

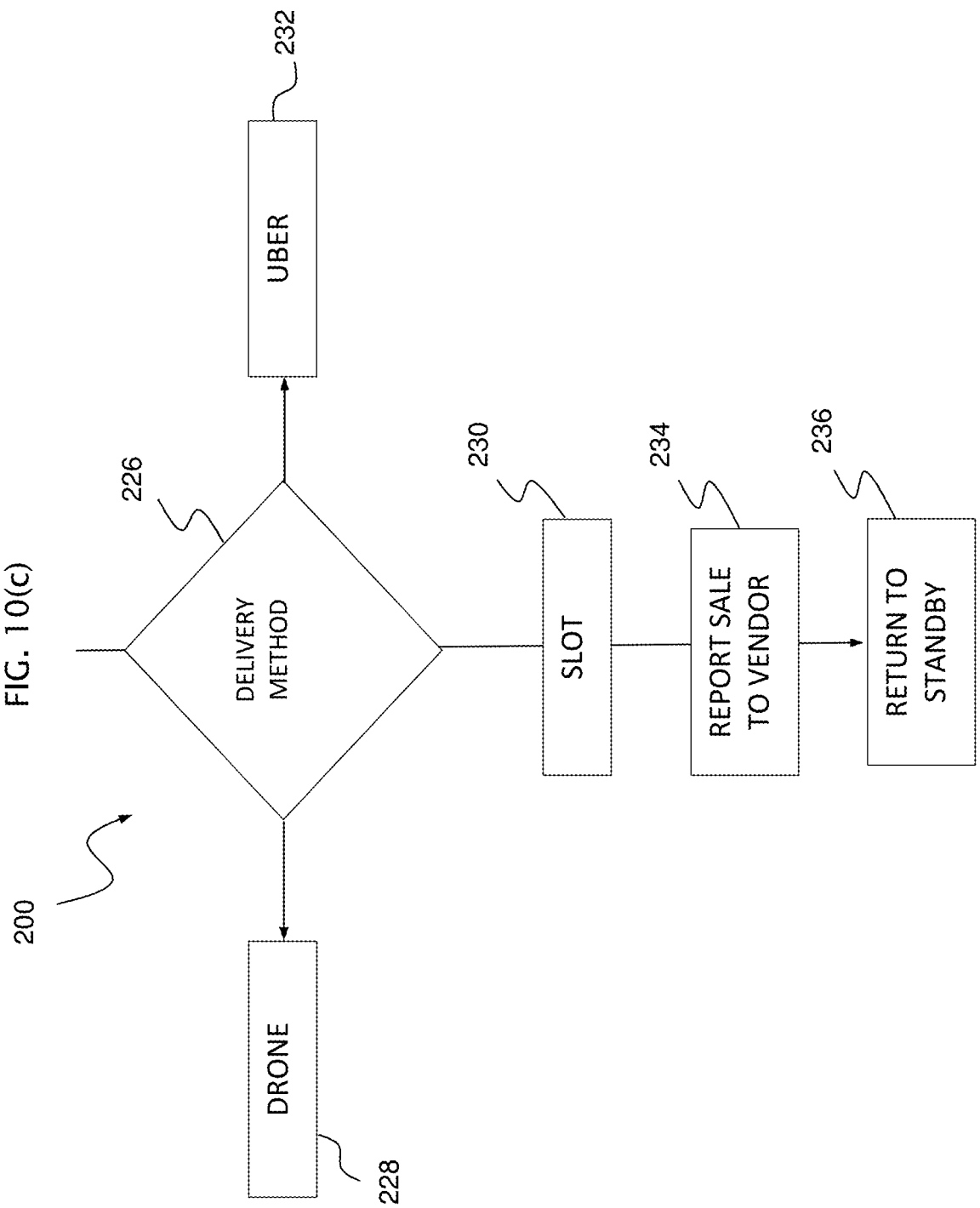

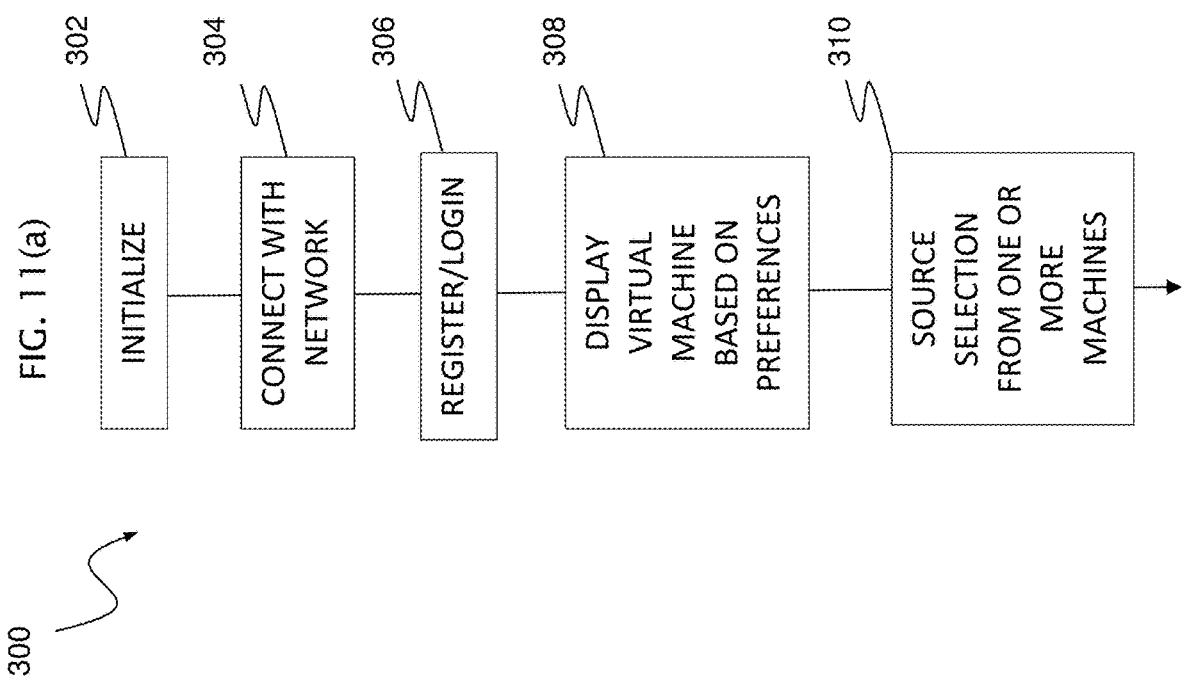

NETWORKED AUGMENTED REALITY AND VIRTUAL VENDING MACHINE

BACKGROUND OF THE INVENTION

Field of the Invention

The present invention relates to electrical and mechanical systems. More specifically, the present invention relates to vending machines.

Description of the Related Art

Vending machines are well-known in the art. As noted by Wikipedia: "A vending machine is an automated machine that provides items such as snacks, beverages, alcohol, cigarettes and lottery tickets to consumers after money or a credit card is inserted into the machine. The first modern vending machines were developed in England in the early 1880s that dispensed postcards. Vending machines exist in many countries, and in more recent times, specialized vending machines that provide less common products compared to traditional vending machine items have been created and provided to consumers." https://en.wikipedia.org/wiki/Vending_machine.

Accordingly, conventional vending machines require the user to be physically present at the machine to select, pay for and receive product. For some users, this requirement imposes a significant restraint or inconvenience on the user.

Hence, for such users, there was a need in the art for an intelligent vending machine that does not require the user to be physically present to select, pay for or receive products purchased from the machine.

The need in the art is addressed by copending patent application filed Mar. 5, 2018 by C. Bryant entitled Networked Vending Machine With Drone Based Delivery and Augmented Reality Viewing Systems, Ser. No. 15/912,316 the teachings of which are hereby incorporated herein by reference. This application discloses and claims many novel features.

However, the need remains in the art for an improved system for implementing a more intelligent and accessible vending machine at low cost.

SUMMARY OF THE INVENTION

The need in the art is addressed by the system of the present invention. In the illustrative embodiment, the invention includes a first system for maintaining an inventory of goods available for purchase and providing images relating thereto; a second system for wirelessly communicating the images to a mobile communications and computing platform; a third system operationally coupled the mobile communications and computing platform for displaying on the mobile platform at least one of the images of one of the goods on the platform in response to a user's navigation; and a fourth system for effecting a purchase transaction with respect to at least one of the goods correlated with the displayed image.

In the augmented reality embodiment, navigation is effected by physically moving the mobile platform relative to the inventive vending machine whereby the products displayed, and the views thereof, change and vary as a function of the relative position of the mobile platform and the vending machine.

As an alternative, the physical vending machine is replaced with a virtual vending machine adapted to display the goods on the user's mobile platform in a three-dimensional space.

The illustrative embodiment of a physical vending machine further includes a housing, a controller mounted within the housing and a physically separate and independent user device (smartphone or tablet) including a processor, memory fixed in a tangible medium and an application programmed to communicate with the vending machine controller to enable a user to view and select product from the vending machine in an augmented reality that allows a user to view images of the contents of the vending machine on a mobile computing and communications platform, whereby the products displayed, and the views thereof, change and vary as a function of the relative position of the mobile platform and the vending machine. The inventive vending machine may be implemented as a kiosk.

In the illustrative embodiment, the vending machine has a pattern or symbols one at least one surface thereof adapted to be sensed by a camera on the mobile platform. The mobile application includes code for converting the symbols into product images. These product images are transmitted to the mobile platform by the vending machine. As an alternative, the product images are transmitted to the mobile platform from an external database by a controller via a wide area network.

In an alternative embodiment, the vending machine further includes a system for detecting proximity of a user and activating voice activation functionality in response thereto. In another embodiment, the machine dispenses knowledge via the mobile platform, regarding how the selection might affect the user or patient, how it should be used etc. In the embodiment, the system includes an arrangement for checking a user's ID or prescription.

In another alternative embodiment, a virtual vending machine for storing and transmitting images of products in inventory to a user is disclosed including: a controller including a processor; memory fixed in a tangible medium for execution by the controller to output a display of a virtual vending machine to a user showing products located in plural separate locations using a virtual reality system; and a network server operationally coupled to the controller and to a user device via a wide area network. In this case, the user's mobile platform includes an application adapted to communicate with the controller via the network server to view and select product from the virtual vending machine. The inventive system allows users to browse the virtual machine in three dimensions, not just a 3D view of product, but rows and columns of products in each window or category. A user can hold smartphone in the air anywhere and see into a virtual machine via the network. Each product may be replaced by a video or text or other graphic information. Delivery may be achieved via a physical machine directly, via conventional delivery such as by a network of connected vehicles (e.g. Uber) or via a drone.

BRIEF DESCRIPTION OF THE DRAWINGS

FIG. 1 is a frontal view of a vending machine system in accordance with the teachings of the above-noted Bryant application.

FIG. 2 is a frontal view of an illustrative embodiment of a vending machine system in accordance with the present teachings.

FIG. 3 is a frontal view of the vending machine of FIG. 2 showing operation when a user's mobile computing and communications platform is in a first position relative to the machine.

FIG. 4 is a frontal view of the vending machine of FIG. 2 showing operation when a user's mobile computing and communications platform is in a second position relative to the machine.

FIG. 5 is a block diagram of an illustrative embodiment of electronic circuitry of a network provided by the vending machine of the present teachings.

FIG. 6 is a block diagram of an illustrative embodiment of electronic circuitry of an AR interface provided by the vending machine of the present teachings.

FIG. 7 is a block diagram of an illustrative embodiment of electronic circuitry of a user's mobile computing and communications platform in accordance with an AR embodiment of the present teachings.

FIG. 8 is a block diagram of an illustrative embodiment of electronic circuitry of a VR interface provided by the vending machine of the present teachings.

FIG. 9 is a block diagram of an illustrative embodiment of electronic circuitry of a user's mobile computing and communications platform in accordance with a VR embodiment of the present teachings.

DESCRIPTION OF THE INVENTION

Figure 10A:
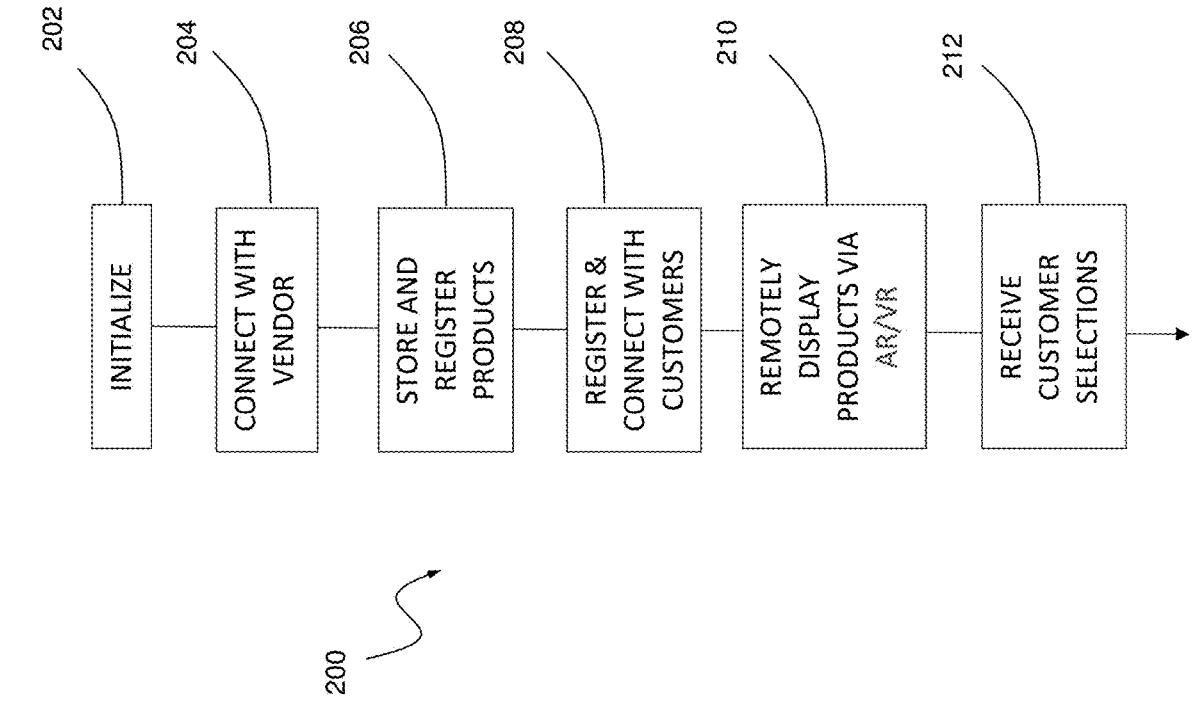
FIGS. 10(a-c) show a flow diagram of an illustrative embodiment of an operational method of a vending machine network implemented in accordance with the present teachings.

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

FIG. 1 is a frontal view of a vending machine system in accordance with the teachings of the above-noted Bryant application. As shown in FIG. 1, the vending machine 20 includes a housing 21 and plural physical and/or virtual windows 22 (of which 12 are shown in the drawings for the purpose of illustration) for displaying products available for purchase via the machine 20. Conventionally, each physical window 22 is a simple transparent glass or plastic window. In accordance with the Bryant teachings, one or more of the windows is a digital display of products available in the machine and hence 'virtual'. A reader 24 is provided for accepting currency of all currently known types including cash, credit and debit cards and crypto (aka 'digital') currency. A user display 26 is also mounted on the control panel 27 of the machine 20. Purchased product is dispensed to the consumer via a conventional slot 28.

FIG. 2 is a frontal view of an illustrative embodiment of a vending machine 10 in accordance with the present teachings In this embodiment, the windows, displays and reader are replaced by an electronic system, mounted within a housing 9 of the vending machine 10 or outside the vending machine 10 and otherwise operationally coupled to the user's mobile platform, that enables a consumer to view and purchase product via a smartphone, tablet or other mobile computing and communications platform.

Those of ordinary skill in the art will appreciate the prospect for significantly reduced design, manufacturing and maintenance cost associated with the significantly simplified design of a vending machine in accordance with the present teachings. The operation of the vending machine of FIG. 2 is illustrated in FIGS. 3 and 4.

FIG. 3 is a frontal view of the vending machine of FIG. 2 showing operation when a user's mobile computing and communications platform is in a first position 'A' relative to the machine 10. In accordance with the present teachings, in an onsite (within wireless proximity of the physical vending machine 10) augmented reality (AR) mode of operation, the position and orientation of a mobile communications and computing platform 12 are detected by the machine 10 or output by the platform 12 using conventional internal position (GPS), orientation (three axis accelerometer) and altitude sensors.

As another alternative, symbols may be placed on the face plate 11 of the machine 10 which are read by a camera on the mobile platform and used to ascertain position of the mobile platform 12 relative to the face plate 11. This may be accomplished with an application running on the smartphone as a software program stored in physical tangible memory (not shown) which, when executed by the onboard processor (not shown) reads and interprets the symbols on the face plate to ascertain a unique machine serial number and the instantaneous location of the mobile platform in x.y.z linear coordinates and angular $\alpha$, $\theta$, $\varphi$ angular coordinates.

As discussed more fully below, this position and orientation data is used by the system 10 to communicate to the platform 12, navigate within the virtual reality space therein and display images of products 14 associated with a predetermined physical or virtual location within the machine 10.

FIG. 4 is a frontal view of the vending machine of FIG. 2 showing operation when a user's mobile computing and communications platform is in a second position B relative to the machine 10 at which product 16 is viewable and available for purchase. Hence, as illustrated in FIGS. 3 and 4, as the consumer moves his or her smartphone or tablet over the surface of the faceplate 11, the consumer is able to view products available for purchase from the vending machine on their smartphone that are correlated to the position of the smartphone or tablet relative to the faceplate thereby providing a 'virtual window' into the vending machine 10.

After the consumer makes a selection, payment options are presented via the mobile platform allowing for the product to be purchased and dispensed from the machine 10 via slot 28.

FIG. 5 is a block diagram of an illustrative embodiment of electronic circuitry of a network provided by the vending machine of the present teachings. Bus lines showing electrical and operational connections between elements are omitted herein for simplicity and clarity. However, those of ordinary skill in the art will appreciate that electrical and operational connections would be required for proper operation in accordance with the teachings below.

At the core of the vending machine system 10 is a controller 40 implemented, in the best mode, with a microprocessor or group of processors. The controller 40 executes a program stored a tangible mechanical or electronic storage medium 62.

In a networked implementation, the controller 40 communicates in a conventional manner with the retailer system 34 and database 36 via a network server 42, WIFI or coax interface 52 and a wide area network 50, such as the World Wide Web or Internet, via internet interface 44. The controller 40 communicates with users' mobile platforms 12 via a Bluetooth interface 48 in a conventional manner. The network server 42 provides bidirectional communications protocols needed for the interfaces 44, 48 and 52 to communicate with the controller 40.

Onsite maintenance personnel inputs are provided to the controller 40 by a conventional input/output (I/O) interface 70 such as a keyboard and pointing device. A setup display 72 is provided for onsite use by maintenance personnel as well. Optional rear and front facing cameras 68, 69 are included. The rear facing camera 68 would be coupled to the controller 40 for capturing images of the products stored in the vending machine 10 or symbols associated therewith for use with the augmented reality interface 54. The optional front facing camera 69 may be included for consumer identity confirmation.

In accordance with the present teachings, an augmented reality (AR) interface 54 and a virtual reality (VR) interface 56 are included in the system 10.

FIG. 6 is a block diagram of an illustrative embodiment of electronic circuitry of an AR interface 54 of the vending machine 10 of the present teachings. As shown in FIG. 6, in the illustrative embodiment, the AR interface 54 includes an AR controller 74. The AR controller 74 may be implemented with a separate processor or in software adapted to be executed by the controller 40 of FIG. 5.

The AR controller 74 correlates product inventory available in or to the machine 10 (shown generally at 76) with two-dimensional or three-dimensional images stored in memory 62. The controller 74 presents an image or object to a user platform 12 for display at predetermined position and orientation based on the position and orientation of the user platform 12. The position or orientation of the user platform 12 may be detected by conventional smartphone position, orientation and altitude sensors (not shown) internal to the platform 12. For more accuracy, the position and orientation of the user's smartphone 12 may be calculated by using the onboard camera to detect images, symbols or other markers on the face plate 11 of the vending machine 10.

The position and orientation data are sent by the smartphone 12 to the AR controller 74 via the Bluetooth interface 48 or the WIFI interface 52.

FIG. 7 is a block diagram of an illustrative embodiment of electronic circuitry of a user's mobile computing and communications platform 12 in accordance with an AR embodiment of the present teachings In accordance with the present teachings, an AR controller application 80, stored in onboard tangible electronic memory (not shown) receives input from onboard camera 82 and location, orientation and position sensors 84 and uploads the corresponding data to the AR interface 54 of FIGS. 5 and 6. In response to this data, as mentioned above, the AR interface 54 returns imagery to the AR controller application 80 for presentation via an onboard display 86. Thus, tilting the platform forward could translate to forward movement, tilting backward could translate to backward movement, tilting or moving left would move left and tilting or moving right would move right. These movements could be used in the virtual vending machine embodiment discussed more fully below. User input and output at the smartphone 12 are provided via I/O 87. A currency payment module is included and coupled to the controller 80.

The AR embodiment might be preferred for applications where the vending machine is dispensing product from the machine, a store or a warehouse directly to a consumer. As an alternative, in accordance with the present teachings, a VR embodiment is enabled by which product is aggregated from inventory that may be distributed via numerous machines, stores and/or warehouses and delivered to the consumer via one or more delivery vehicles including drones or automobile delivery services such as Uber or Lyft.

In accordance with the present teachings, the virtual vending machine embodiment is an integral component in a network that may include one or more vending machines (mobile or stationary), warehouses, stores, retailers', databases and plural customer devices. This is disclosed more fully below.

FIG. 8 is a block diagram of an illustrative embodiment of electronic circuitry of a VR interface provided by the vending machine of the present teachings. The VR interface includes a VR controller 90. As is the case with the AR application controller 74 of FIG. 6, the VR controller 90 may be implemented with a separate processor or in software adapted to be executed by the controller 40 of FIG. 5.

The VR controller 90 correlates product inventory available that may be distributed via numerous machines, stores and/or warehouses (shown generally at 77) with three-dimensional objects or images stored in memory 62 or live video camera feeds of actual products such as produce. The VR controller 90 sends this image, object or video stream to the user smartphone 12 for display at predetermined position based on the user's navigation in within a virtual machine that displays 3D representations of available products on the user's smartphone 12. Authentication and registration are handled by a first module 92 and financial transactions are handled by an ecommerce system 93.

FIG. 9 is a block diagram of an illustrative embodiment of electronic circuitry of a user's mobile computing and communications platform in accordance with a VR embodiment of the present teachings. The network interface 78 discussed above with reference to FIG. 7 couples the data received from a virtual vending machine via the wide area (e.g. Internet) network 50 of FIG. 5 a VR controller application 94. In accordance with the present teachings, the VR controller application 94, stored in onboard tangible electronic memory (not shown) receives input from onboard location, orientation and position sensors 84 and uploads the corresponding data to the VR interface 56 of FIGS. 5 and 8. In response to this data, the VR interface 56 returns imagery to the VR controller application 94 for presentation via an onboard display 86.

As noted above, tilting the platform forward could translate to forward movement, tilting backward could translate to backward movement, tilting or moving left would move left and tilting or moving right would move right. Thus, from any location, the consumer could shop via his or her smartphone or tablet, as though physically present in an actual store as opposed to a simple vending machine. For the vision impaired, a voice activated and controlled assistant could describe the products being viewed and assist in consummating the transaction.

User input and output at the smartphone 12 are provided via I/O 87. A currency payment interface 88 is included and coupled through the controller 94 to the authentication and registration module 92 and the ecommerce module 93 of the virtual vending machine interface 56 of FIG. 8.

FIGS. 10(*a-c*) show a flow diagram of an illustrative embodiment of an operational method of a vending machine network implemented in accordance with the present teachings. At step 202, the system 10 is initialized. A vendor connects to the system 10 and registers product information as being available for purchase from vending machines implemented in accordance with the present teachings or a warehouse. These steps are shown generally at 204 and 206 in FIG. 10. At step 208, a consumer registers for virtual access to the system.

At step 210, the user views the content of a virtual vending machine via an AR interface 54 or VR interface 56 both of which are discussed above.

At step 212, the consumer makes a selection and at step 214, the system 10 processes the payment transaction by initially prompting the user or consumer to select currency type.

At step 216, the consumer's currency type selection is received and used to process the transaction in the manner discussed more fully above with respect to onsite, physical vending machine operational mode.

After payment, at step 224, the selected product is dispensed for pickup or delivery. If at step 226, 'pickup' is selected, then at step 230, the selected product is dispensed to the consumer via the slot 28 (FIG. 2).

At step 234, sales are optionally credited and/or reported to the vendor (retailer 34) of the product via the controller 40, network server 42, internet interface 44 and network 50 for inventory control, marketing purposes and/or other purposes. See FIG. 5.

At step 236, the system returns to standby mode.

Consumer Platform:

In the best mode, the consumer platform is implemented with an iPhone, Android or other comparable smartphone, tablet or computing and communications platform.

Figure 11B:
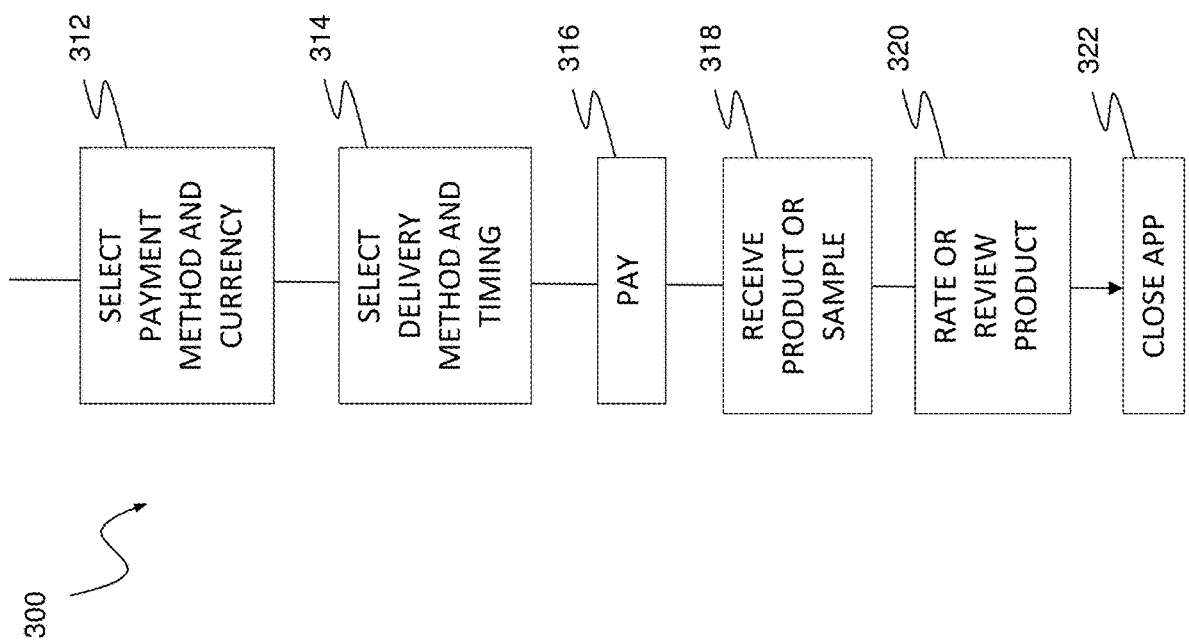
FIGS. 11(a-b) show a flow diagram of an illustrative embodiment of an operational method of a user's device in a network implemented in accordance with the present teachings.

FIGS. 11(*a-b*) show a flow diagram of an illustrative embodiment of an operational method of a user's device in a network implemented in accordance with the present teachings. As shown in FIGS. 11(*a-b*), the method 300 includes a first initializing step. This would typically involve downloading and launching a program or application (aka 'app') designed to communicate within the network 100 of FIG. 5.

At step 304, the app connects with the network 100 and at step 306, the user either registers or logs in if already registered.

At step 308, the user selects desired product types and is presented by the app with a display of a virtual vending machine in which plural units of the desired product type(s) from various vendors is/are displayed on the user's smartphone. In accordance with the present teachings, the movement of the user's smartphone changes the display of products as if the smartphone is a window into the virtual vending machine. As discussed above, this may be facilitated using gyros, accelerometers, GPS and other location and orientation sensors commonly provided in conventional smartphones along with symbols and/or other markers on the vending machine to assist in location determination.

Those skilled in the art will appreciate that, as an alternative, a headset may also be used to view the contents of the virtual vending machines without departing from the scope of the present teachings.

In any case, at step 310, the user selects products for purchase and delivery and at step 312, payment method and currency are selected. As noted above, the user's identification (ID) may be confirmed automatically via biometric sensors in the smartphone such as the fingerprint or face sensors of the iPhone or manually via video conference with a retailer.

At step 314, the delivery method and timing are selected and at step 316, payment is effectuated. The user receives the product, or perhaps a sample, at step 318 and at step 320, the user is invited to rate or review the product.

Thus, the inventive system provides a vending machine with a controller and a user device including a processor, memory fixed in a tangible medium and an application programmed to communicate with the controller to enable a user to view and select product from the vending machine in an augmented reality that allows a user to view images of the contents of the vending machine on a mobile computing and communications platform, whereby the products displayed, and the views thereof, change and vary as a function of the relative position of the mobile platform and the vending machine. The inventive vending machine may be implemented as a kiosk.

In the illustrative embodiment, the vending machine has a pattern or symbols one at least one surface thereof adapted to be sensed by a camera on the mobile platform. The mobile application includes code for converting the symbols into product images. These product images are transmitted to the mobile platform by the vending machine. As an alternative, the product images are transmitted to the mobile platform from an external database by a controller via a wide area network.

In an alternative embodiment, the vending machine further includes a system for detecting proximity of a user and activating voice activation functionality in response thereto. In another embodiment, the machine dispenses knowledge via the mobile platform, regarding how the selection might affect the user or patient, how it should be used etc. In the embodiment, the system includes an arrangement for checking a user's ID or prescription.

In another alternative embodiment, a virtual vending machine for storing and transmitting images of products in inventory to a user is disclosed including: a controller including a processor; memory fixed in a tangible medium for execution by the controller to output a display of a virtual vending machine to a user showing products located in plural separate locations using a virtual reality system; and a network server operationally coupled to the controller and to a user device via a wide area network. In this case, the user's mobile platform includes an application adapted to communicate with the controller via the network server to view and select product from the virtual vending machine. The inventive system allows users to browse the virtual machine in three dimensions, not just a 3D view of product, but rows and columns of products in each window or category. A user can hold smartphone in the air anywhere and see into a virtual machine via the network. Each product may be replaced by a video or text or other graphic information. Delivery may be achieved via a physical machine directly, via conventional delivery such as by a network of connected vehicles (e.g. Uber) or via a drone.

Voice activation functionality is enabled at the physical vending machine and via a user's smartphone. The system is adapted to provide detailed information, via a user's smartphone or an onsite display integrated into the vending machine, regarding how the selection might affect the user/patient, how it should be used and/or how it has been rated by other users/patients. In a particularly unique embodiment, the inventive system includes an application adapted to run on a user's smartphone that provides access for the vision impaired through voice activation, checks the user's biometric data and/or confirms the user's identity.

The vending machine may be a stand-alone machine or built into the wall with an open back allowing for manual or automated stocking with either individual goods or bundles of goods. In this case, the user's mobile platform can be used to display products available in the store or warehouse as opposed to merely what is available in or at the vending machine per se.

Those having ordinary skill in the art and access to the present teachings will recognize additional modifications, applications and embodiments within the scope thereof.

It is therefore intended by the appended claims to cover any and all such applications, modifications and embodiments within the scope of the present invention.

The invention claimed is:

1. A system comprising:
    a first system for maintaining an inventory of goods available for purchase and providing images relating thereto;
    a second system for wirelessly communicating the images to a mobile communications and computing platform;
    a third system operationally coupled the mobile communications and computing platform for displaying on the mobile platform at least one of the images of one of the goods on the platform in response to a user's navigation, wherein the navigation is effected by physically moving the platform such that the third system provides a virtual vending machine adapted to display the goods in a three-dimensional space; and
    a fourth system for effecting a purchase transaction with respect to at least one of the goods correlated with the displayed image.

2. The invention of claim 1 wherein third system includes code stored in tangible memory and executed by a processor for enabling navigation within the three-dimensional space.

3. The invention of claim 1 wherein the system is a vending machine having:
    a first controller and
    a dispenser for delivering goods purchased by a customer.

4. The invention of claim 3 wherein the mobile platform includes:
    a mobile platform processor,
    memory fixed in a tangible medium and
    an application programmed to enable the platform processor to communicate with the vending machine controller to enable a user to view and select product from the vending machine in an augmented reality that shows a user to view images of the contents of the vending machine on the mobile computing and communications platform.

5. The invention of claim 4 whereby the products displayed, and the views thereof, change and vary as a function of the relative position of the mobile platform and the vending machine.

6. The invention of claim 5 wherein the vending machine has symbols on at least one surface thereof adapted to be sensed by a camera on the mobile platform.

7. The invention of claim 6 wherein the application includes code for converting the symbols into product images.

8. The invention of claim 7 wherein the product images displayed as a function of the symbols are transmitted to the mobile platform by the vending machine.

9. The invention of claim 8 wherein the product images displayed as a function of the symbols are transmitted to the mobile platform from an external database by a controller via a wide area network.

10. The invention of claim 1 wherein the vending machine further includes a system for detecting proximity of a user and activating voice activation functionality.

11. The invention of claim 1 wherein the machine dispenses knowledge, via the smartphone, regarding how the selection might affect the user/patient, how it should be used and how it has been rated by other users/patients.

12. The invention of claim 1 wherein the system includes an arrangement for checking a user's ID or prescription.

13. The invention of claim 1 wherein the system includes an arrangement for checking a user's biometric data.

14. The invention of claim 1 wherein the application provides access for the vision impaired through voice activation.

15. A vending machine comprising:
    a housing
    a first system mounted at least partially within the housing for receiving data regarding goods available for purchase and providing images relating thereto;
    a second system for wirelessly communicating the images to a mobile communications and computing platform;
    a third system within the mobile communications and computing platform for displaying on the mobile platform at least one of the images of one of the goods on the platform in response to a user's navigation, wherein the navigation is effected by physically moving the platform such that the third system provides a virtual vending machine adapted to display the goods in a three-dimensional space; and
    a fourth system mounted within the vending machine and the platform for effecting a purchase transaction with respect to at least one of the goods correlated with the displayed image.

16. The invention of claim 15 wherein the vending machine includes:
    a first controller and
    a dispenser for delivering goods purchased by a customer.

17. The invention of claim 15 wherein the mobile platform includes:
    a mobile platform processor,
    memory fixed in a tangible medium and
    an application programmed to enable the platform processor to communicate with the vending machine controller to enable a user to view and select product from the vending machine in an augmented reality that shows a user to view images of the contents of the vending machine on the mobile computing and communications platform.

* * * * *